(12) United States Patent
Lin et al.

(10) Patent No.: US 11,965,898 B2
(45) Date of Patent: Apr. 23, 2024

(54) AUTOMATIC NUCLEIC ACID DETECTION SYSTEM AND METHOD THEREOF

(71) Applicants: TCI Co., Ltd., Taipei (TW); TCI GENE INC, Taipei (TW)

(72) Inventors: Yung-Hsiang Lin, Taipei (TW); Cheng-Hong Hsieh, Taipei (TW); Ciao-Ting Chen, Taipei (TW); Tsung-Cheng Chen, Taipei (TW)

(73) Assignees: TCI GENE INC, Taipei (TW); TCI CO., LTD, Taipei (TW)

( * ) Notice: Subject to any disclaimer, the term of this patent is extended or adjusted under 35 U.S.C. 154(b) by 847 days.

(21) Appl. No.: 16/936,810

(22) Filed: Jul. 23, 2020

(65) Prior Publication Data

US 2021/0302448 A1 Sep. 30, 2021

Related U.S. Application Data

(60) Provisional application No. 63/000,667, filed on Mar. 27, 2020.

(30) Foreign Application Priority Data

Jun. 12, 2020 (TW) .................................. 109119920

(51) Int. Cl.
*G01N 35/10* (2006.01)
*B01L 3/00* (2006.01)
(Continued)

(52) U.S. Cl.
CPC ...... *G01N 35/00613* (2013.01); *B01L 3/5021* (2013.01); *B01L 3/50825* (2013.01);
(Continued)

(58) Field of Classification Search
CPC ....... B01L 2200/143; B01L 2200/0261; B01L 2200/0531; B01L 2300/021;
(Continued)

(56) References Cited

U.S. PATENT DOCUMENTS

| 5,985,214 A * | 11/1999 | Stylli ................. G01N 35/1002 700/214 |
| 2002/0090320 A1* | 7/2002 | Burow .................... B01L 9/523 422/561 |
| 2005/0196867 A1* | 9/2005 | Bower ............. G01N 35/00603 436/43 |

(Continued)

FOREIGN PATENT DOCUMENTS

| CN | 110050070 A | 7/2019 |
| CN | 110564607 A | 12/2019 |

(Continued)

OTHER PUBLICATIONS

European Search Report from corresponding European Application No. 20187530.9 dated Dec. 10, 2020, 7 pages.
(Continued)

*Primary Examiner* — Jill A Warden
*Assistant Examiner* — Dwayne K Handy
(74) *Attorney, Agent, or Firm* — Christensen, Fonder, Dardi & Herbert PLLC

(57) ABSTRACT

An automatic nucleic acid detection system and a method thereof are disclosed. The automatic nucleic acid detection method includes: performing, by an automatic control subsystem, on a nucleic acid extraction machine platform, a nucleic acid extraction on one or more specimens in a sample tray to generate one or more corresponding nucleic acids in the sample tray; distributing, by the automatic control subsystem, on a nucleic acid distribution machine platform, the nucleic acid in each hole of the sample tray and a first reagent into a plurality of holes of a detection tray, wherein the number of holes of the detection tray is greater than that of the sample tray; and performing, by the automatic control subsystem, on a nucleic acid detection machine platform, a nucleic acid detection on the detection tray.

20 Claims, 8 Drawing Sheets

(51) Int. Cl.
*B01L 7/00* (2006.01)
*G01N 35/00* (2006.01)

(52) U.S. Cl.
CPC ............ *B01L 3/50857* (2013.01); *B01L 3/52* (2013.01); *B01L 3/5453* (2013.01); *B01L 3/5457* (2013.01); *B01L 7/525* (2013.01); *G01N 35/10* (2013.01); *B01L 2200/10* (2013.01); *B01L 2200/143* (2013.01); *B01L 2200/16* (2013.01); *B01L 2300/021* (2013.01); *B01L 2300/04* (2013.01); *B01L 2300/0663* (2013.01)

(58) Field of Classification Search
CPC .......... B01L 2300/022; B01L 2200/16; G01N 35/00613; G01N 35/00732; G01N 35/0099; G01N 2035/00801; G01N 2035/00821; G01N 2035/00831; G01N 2035/00841; G01N 35/10; G01N 35/1002; G01N 35/1065; G01N 2035/1076
See application file for complete search history.

(56) References Cited

U.S. PATENT DOCUMENTS

| | | |
|---|---|---|
| 2009/0130679 A1 | 5/2009 | Wu et al. |
| 2013/0331298 A1 | 12/2013 | Rea |
| 2016/0003791 A1* | 1/2016 | Lebedev ............... G01N 33/15 422/68.1 |
| 2016/0319329 A1 | 11/2016 | Natale et al. |
| 2019/0316179 A1 | 10/2019 | Day et al. |

FOREIGN PATENT DOCUMENTS

| | | | |
|---|---|---|---|
| CN | 110702933 A | 1/2020 | |
| TW | I271218 B | 1/2007 | |
| TW | I275643 B | 3/2007 | |
| WO | WO 00/060362 | * 10/2000 | ............ G01N 35/02 |

OTHER PUBLICATIONS

Office Action issued on Dec. 27, 2023 by China National Intellectual Property Administration (CNIPA) to the Chinese counterpart.

* cited by examiner

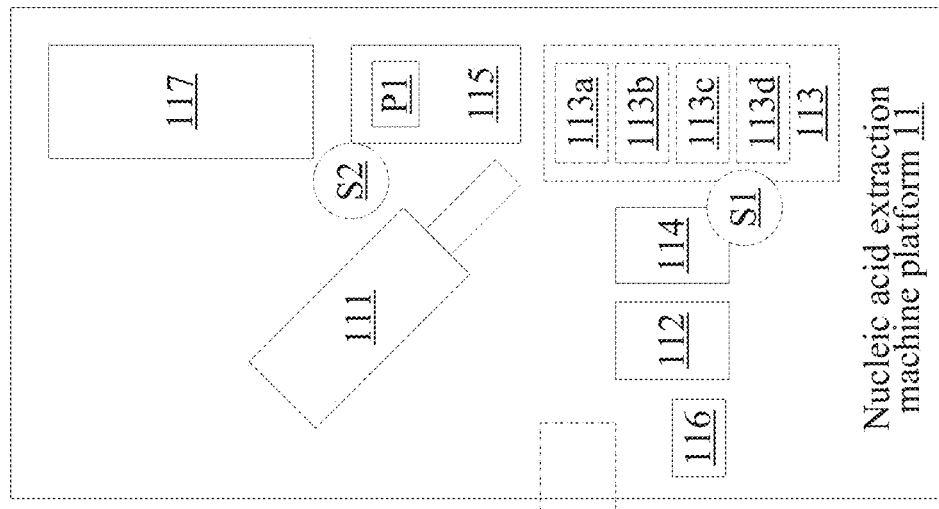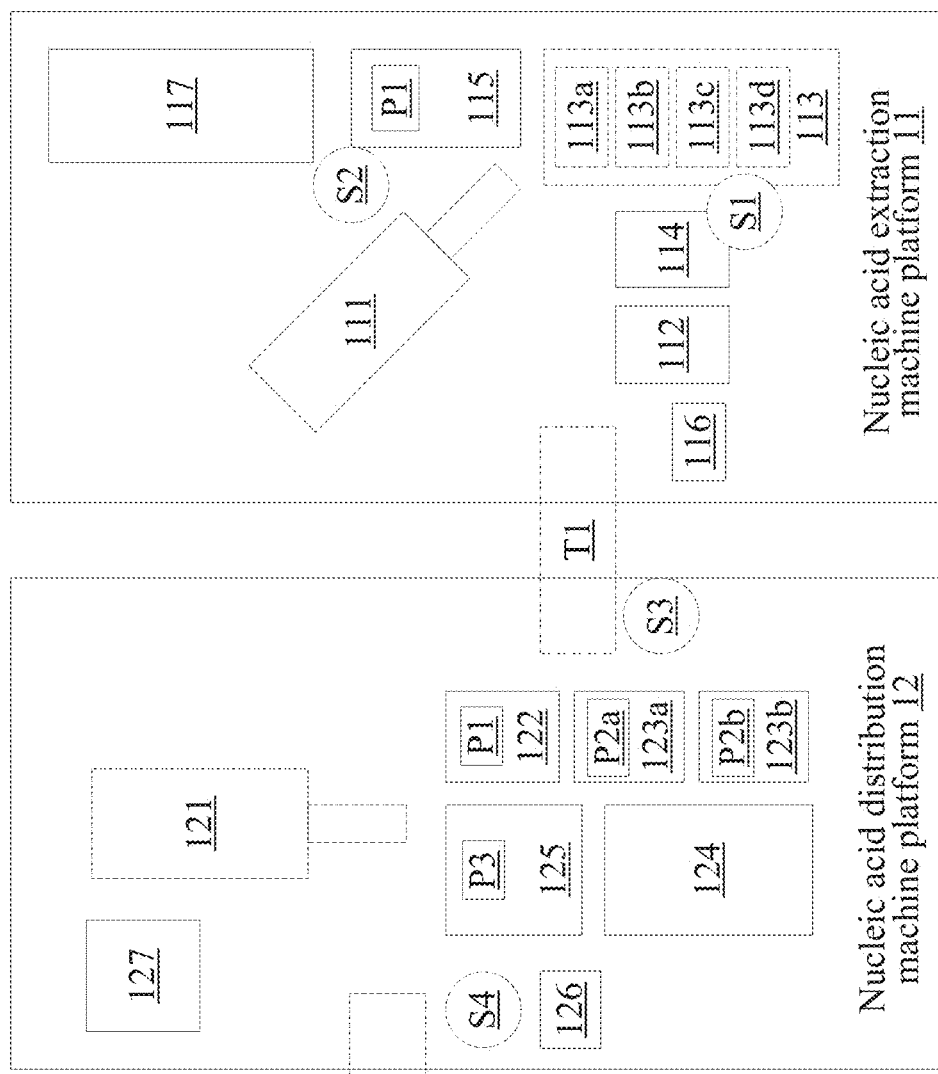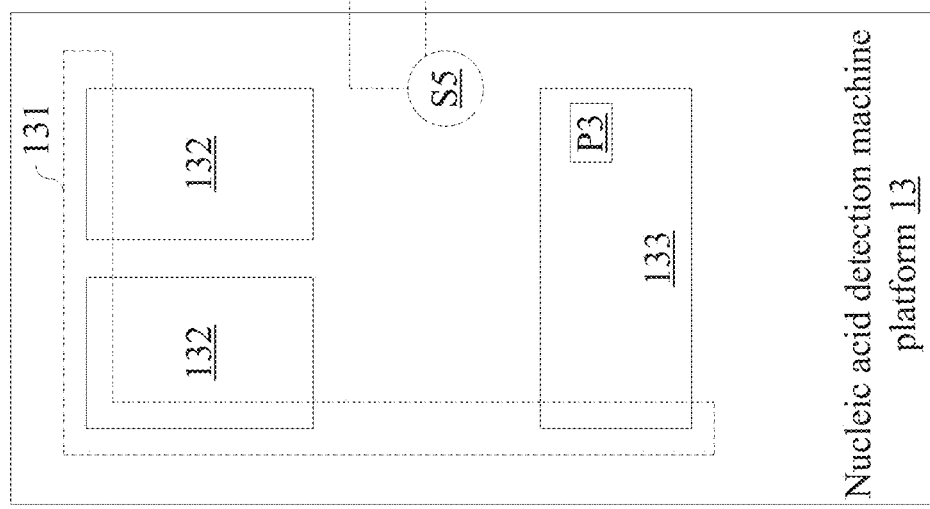
FIG. 2

```
                                                    ┌─ 5
                                                    │
                                                    ▼

┌──────────────────────────────────────────────┐
│ Performing, by an automatic control          │ ┌─ 501
│ subsystem, on a nucleic acid extraction      │
│ machine platform, nucleic acid extraction    │
│ on one or a plurality of specimens in a      │
│ sample tray to generate one or a plurality   │
│ of corresponding nucleic acids in the        │
│ sample tray                                  │
└──────────────────────────────────────────────┘
                        │
                        ▼
┌──────────────────────────────────────────────┐
│ Distributing, by the automatic control       │ ┌─ 502
│ subsystem, on a nucleic acid distribution    │
│ machine platform, the nucleic acid in each   │
│ hole of the sample tray and a first reagent  │
│ into a plurality of holes of a detection     │
│ tray, wherein the number of holes of the     │
│ detection tray is greater than the number    │
│ of holes of the sample tray                  │
└──────────────────────────────────────────────┘
                        │
                        ▼
┌──────────────────────────────────────────────┐
│ Performing, by the automatic control         │ ┌─ 503
│ subsystem, on a nucleic acid detection       │
│ machine platform, nucleic acid detection     │
│ on the detection tray                        │
└──────────────────────────────────────────────┘
```

FIG. 5

AUTOMATIC NUCLEIC ACID DETECTION SYSTEM AND METHOD THEREOF

CROSS-REFERENCES TO RELATED APPLICATIONS

This application claims priority to Taiwan Patent Application No. 109119920, filed on Jun. 12, 2020, and U.S. Provisional Patent Application No. 63/000,667, filed on Mar. 27, 2020. Taiwan Patent Application No. 109119920 and U.S. Provisional Patent Application No. 63/000,667 are incorporated herein by reference in their entireties.

BACKGROUND OF THE INVENTION

Field of the Invention

Embodiments of the present invention relate to a nucleic acid detection system and method. More specifically, embodiments of the present invention relate to an automatic nucleic acid detection system and method.

Descriptions of the Related Art

Nucleic acid detection may be applied to detect whether viruses exist in a specimen or not. The conventional nucleic acid detection process comprises: extracting nucleic acids from a plurality of specimens to be detected in a plurality of holes in a sample tray by a nucleic acid extraction device, manually mixing the extracted nucleic acids with a first reagent (e.g., a reagent for detection (i.e., a reactant)) and injecting the mixture into holes in a detection tray, and performing fluorescent quantitative analysis on the nucleic acids mixed with the first reagent in the detection tray by a nucleic acid detection device to detect whether the nucleic acids contain viruses.

According to characteristics of certain viruses, a plurality of gene loci may be required in order to confirm the presence of viruses in a certain specimen (i.e., a plurality of nucleic acids of the same specimen need to be mixed with the first reagent individually to generate a plurality of corresponding samples, and only if the plurality of samples are all positive for a certain kind of virus, will it represent that the specimen contains the viruses). However, the specifications of the conventional sample tray and the detection tray are fixed and consistent (the numbers of holes are the same). That is, when the detection for each specimen in the sample tray needs a plurality of gene loci, it will inevitably take multiple times of detection cycles to complete the detection of all the gene loci since the nucleic acid detection device can only detect the specimens in one detection tray in one detection cycle. In addition, even if only one gene locus is required for one specimen, it is impossible to perform a large amount of nucleic acid detection within one detection cycle because the specifications of the sample tray and the detection tray are fixed and consistent (the numbers of holes are the same).

Therefore, it is difficult to improve the efficiency of the traditional nucleic acid detection, and there is insufficient adaptability to changes in detection items or detection requirements, thus lacking flexibility in use thereof. On the other hand, the conventional nucleic acid extraction procedure, nucleic acid mixing procedure, and nucleic acid detection procedure are separate procedures, and every two procedures must be connected by human operations, and such human operations will also affect the efficiency of nucleic acid detection.

Accordingly, an urgent need exits in the art to improve the efficiency of nucleic acid detection and increase the adaptability to changes in detection items or detection requirements in the nucleic acid detection process.

SUMMARY OF THE INVENTION

In order to solve at least the aforesaid problems, embodiments of the present invention provide an automatic nucleic acid detection method, and the automatic nucleic acid detection method may comprise the following steps: performing, by an automatic control subsystem, on a nucleic acid extraction machine platform, nucleic acid extraction on one or a plurality of specimens in a sample tray to generate one or a plurality of corresponding nucleic acids in the sample tray; distributing, by the automatic control subsystem, on a nucleic acid distribution machine platform, the nucleic acid in each hole of the sample tray and a first reagent into a plurality of holes of a detection tray; and performing, by the automatic control subsystem, on a nucleic acid detection machine platform, nucleic acid detection on the detection tray. The number of holes of the detection tray is greater than the number of holes of the sample tray.

In order to solve at least the aforesaid problems, embodiments of the present invention further provide an automatic nucleic acid detection system. The automatic nucleic acid detection system may comprise a nucleic acid extraction machine platform, a nucleic acid distribution machine platform, a nucleic acid detection machine platform, and an automatic control subsystem. The automatic control subsystem is connected with the nucleic acid extraction machine platform, the nucleic acid distribution machine platform, and the nucleic acid detection machine platform. The automatic control subsystem may be configured to: perform, on the nucleic acid extraction machine platform, nucleic acid extraction on one or a plurality of specimens in a sample tray to generate one or a plurality of corresponding nucleic acids in the sample tray; distribute, on the nucleic acid distribution machine platform, the nucleic acid in each hole of the sample tray and a first reagent into a plurality of holes of a detection tray; and perform, on the nucleic acid detection machine platform, nucleic acid detection on the detection tray. The number of holes of the detection tray is greater than the number of holes of the sample tray.

In order to solve at least the aforesaid problems, embodiments of the present invention further provide an automatic nucleic acid distribution method, and the automatic nucleic acid distribution method may comprise the following steps: providing, by an automatic control subsystem, a sample tray for a nucleic acid distribution machine platform, wherein the sample tray contains the nucleic acid of one or a plurality of specimens; and distributing, by the automatic control subsystem and on the nucleic acid distribution machine platform, the nucleic acid in each hole in the sample tray and a first reagent into a plurality of holes in a detection tray. The number of holes in the detection tray is greater than the number of holes in the sample tray.

In order to solve at least the aforesaid problems, embodiments of the present invention further provide an automatic nucleic acid distribution system, and the automatic nucleic acid distribution system may comprise a nucleic acid distribution machine platform and an automatic control subsystem. The automatic control subsystem is connected with the nucleic acid distribution machine platform. The automatic control subsystem may be configured to: provide a sample tray for the nucleic acid distribution machine platform, wherein the sample tray contains the nucleic acid of one or a plurality of specimens; and distribute, on the nucleic acid distribution machine platform, the nucleic acid in each hole in the sample tray and a first reagent into a plurality of holes in a detection tray. The number of holes of the detection tray is greater than the number of holes of the sample tray.

In the embodiments of the present invention, the number of holes in the detection tray is greater than the number of holes in the sample tray (for example, a detection tray of which the number of holes is two times of that in the sample tray is used). Therefore, when a specimen requires a plurality of (e.g., two) gene loci, the number of holes in the detection tray will be sufficient to accommodate the plurality of gene loci required for all the specimens in the sample tray. In this way, the detection results of all the specimens can be generated in a same detection cycle. In addition, when only one gene loci is required for a specimen, the detection number in one detection cycle can be increased because the number of holes in the detection tray is greater than the number of holes in the sample tray. On the other hand, in the embodiments of the present invention, nucleic acid extraction, nucleic acid distribution, and nucleic acid detection are performed through various automatic subsystems, so the influence of human operations on nucleic acid detection efficiency can be avoided. Accordingly, as compared to the traditional nucleic acid detection, the embodiments of the present invention show that the present invention can improve the nucleic acid detection efficiency and increase the adaptability to changes of detection items or detection requirements in a nucleic acid detection process.

The above content is not intended to limit the scope claimed in the present invention, but merely outlines the technical problems that the present invention can solve, the technical means that can be adopted and the technical effects that can be achieved, so that a person having ordinary skill in the art can preliminarily understand the present invention. The detailed technology and preferred embodiments implemented for the subject invention are described in the following paragraphs accompanying the appended drawings for a person having ordinary skill in the art to well appreciate the features of the claimed invention.

BRIEF DESCRIPTION OF THE DRAWINGS

Attached drawings may assist in explaining various embodiments of the present invention, in which:

FIG. 2 illustrates a schematic view of an internal structure of an automatic nucleic acid detection system according to some embodiments of the present invention;

FIG. 5 is a schematic view of an automatic nucleic acid detection method according to some embodiments of the present invention.

DESCRIPTION OF THE PREFERRED EMBODIMENT

In the following description, the present invention will be explained with reference to embodiments thereof. However, these embodiments are not intended to limit the present invention to the operations, environment, applications, structures, processes, or steps described in these embodiments. For ease of description, contents that are not directly related to the embodiments of the present invention or that can be appreciated without special explanation will be omitted from depiction herein and in the attached drawings. Dimensions of elements and proportional relationships among individual elements in the attached drawings are only exemplary examples but not intended to limit the scope claimed in the present invention. Unless stated particularly, same (or similar) element symbols may correspond to same (or similar) elements in the following description. The number of each element described below may be one or more in the case where it can be implemented, unless otherwise specified.

Terms used in the present disclosure are only used for describing the embodiments and are not intended to limit the scope claimed in the present invention. Singular forms "a" and "an" are also intended to include the plural forms unless the context clearly indicates otherwise. Terms "comprising", "including" and the like indicate the presence of stated features, integers, steps, operations, elements, and/or components, but do not preclude the presence of one or more other features, integers, steps, operations, elements, components, and/or combinations thereof. The term "and/or" includes any and all combinations of one or more associated listed items.

Figure 1:
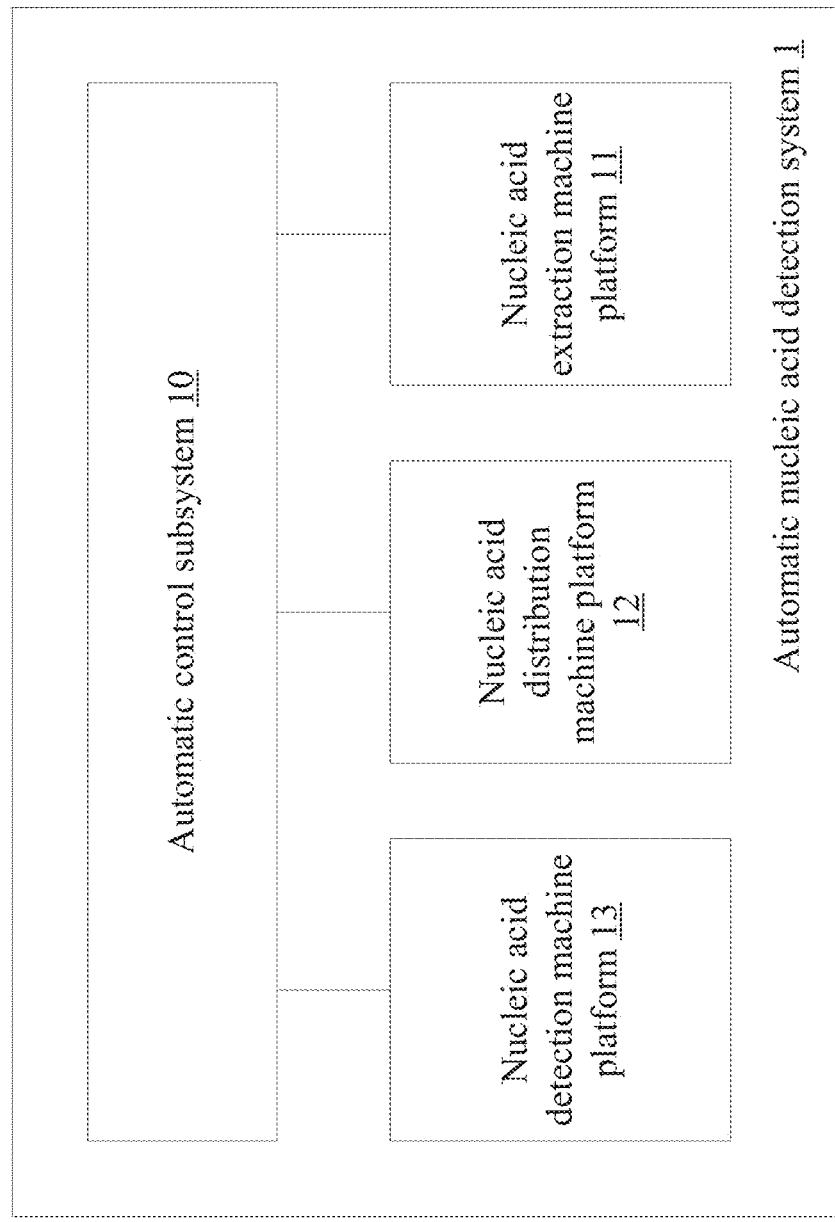
FIG. 1 illustrates a block diagram of an automatic nucleic acid detection system according to some embodiments of the present invention.

FIG. 1 illustrates a block diagram of an automatic nucleic acid detection system according to some embodiments of the present invention. The content shown in FIG. 1 is only for the purpose of illustrating an embodiment of the present invention, and is not intended to limit the scope claimed in the present invention. Referring to FIG. 1, the automatic nucleic acid detection system 1 may basically comprise a nucleic acid extraction machine platform 11, a nucleic acid distribution machine platform 12, a nucleic acid detection machine platform 13, and an automatic control subsystem 10. The automatic control subsystem 10 may be individually connected with the nucleic acid extraction machine platform 11, the nucleic acid distribution machine platform 12 and the nucleic acid detection machine platform 13, and is configured to: perform, on the nucleic acid extraction machine platform 11, nucleic acid extraction on one or a plurality of specimens in a sample tray to generate one or a plurality of corresponding nucleic acids in the sample tray; distribute, on the nucleic acid distribution machine platform 12, the nucleic acid in each hole of the sample tray and a first reagent into a plurality of holes of a detection tray; and perform, on the nucleic acid detection machine platform 13, nucleic acid detection on the detection tray. The number of holes of the detection tray is greater than the number of holes of the sample tray.

Basically, the nucleic acid extraction machine platform 11 is a machine platform on which nucleic acid extraction can be performed, and one or more nucleic acid extraction devices and various devices, equipment, elements or areas related to nucleic acid extraction may be provided and arranged on the machine platform. The nucleic acid detection machine platform 13 is a machine platform on which nucleic acid detection can be performed, and one or more nucleic acid detection devices and various devices, equipment, elements or areas related to nucleic acid detection may be disposed and arranged on the machine platform. The nucleic acid distribution machine platform 12 is a machine platform on which nucleic acid distribution and nucleic acid mixing can be performed, and various devices, equipment, elements or areas related to nucleic acid distribution and nucleic acid mixing may be arranged on the machine platform. The automatic control subsystem 10 includes a computer device and various mechanical devices or elements controlled by the computer device, and these mechanical devices or elements are used to provide functions such as sucking, inserting and taking (tips), griping, moving, and/or sensing. Thus, the automatic control subsystem 10 may control operations related to nucleic acid extraction on the nucleic acid extraction machine platform 11, control operations related to nucleic acid distribution and nucleic acid mixing on the nucleic acid distribution machine platform 12, and control operations related to nucleic acid detection on the nucleic acid detection machine platform 13.

However, in different embodiments of the present invention, the nucleic acid extraction machine platform 11, the nucleic acid distribution machine platform 12, the nucleic acid detection machine platform 13, and the automatic control subsystem 10 may be implemented with different designs. In the following description, elements and operation modes included in the nucleic acid extraction machine platform 11, the nucleic acid distribution machine platform 12, the nucleic acid detection machine platform 13, and the automatic control subsystem 10 according to some embodiments of the present invention will be described by taking FIG. 2, FIG. 3A to FIG. 3C and FIG. 4 as examples, but the contents shown in FIG. 2, FIG. 3A to FIG. 3C and FIG. 4 are not intended to limit the scope claimed in the present invention.

First, FIG. 2 illustrates a schematic view of the internal structure of the automatic nucleic acid detection system 1 according to some embodiments of the present invention. For ease of description, in FIG. 2, the automatic control subsystem 10 is shown in broken lines, and the nucleic acid extraction machine platform 11, the nucleic acid distribution machine platform 12, and the nucleic acid detection machine platform 13 are shown in solid lines.

Referring to FIG. 2, one or more nucleic acid extraction devices 117 may be disposed on the nucleic acid extraction machine platform 11, and a specimen placement area 112, a tip placement area 114, a sample tray placement area 115, and a tip discard area 116 may be arranged on the nucleic acid extraction machine platform 11. One or more centrifuges 127 may be disposed on the nucleic acid distribution machine platform 12, and a sample tray placement area 122, a first reagent placement area 123a, a second reagent placement area 123b, a tip placement area 124, a detection tray placement area 125, and a tip discard area 126 may be arranged on the nucleic acid distribution machine platform 12. One or more nucleic acid detection devices 132 may be disposed on the nucleic acid detection machine platform 13 (two nucleic acid detection devices 132 are illustrated in FIG. 2, but the number thereof is not limited), and a detection tray placement area 133 is arranged on the nucleic acid detection machine platform 13. In addition, the automatic control subsystem 10 may comprise: a computer device (not shown), a first robotic arm 111 disposed on the nucleic acid extraction machine platform 11, a second robotic arm 121 disposed on the nucleic acid distribution machine platform 12, and a third robotic arm 131 disposed on the nucleic acid detection machine platform 13.

According to different requirements, the automatic control subsystem 10 may further comprise one or more specimen container operating devices 113 disposed on the nucleic acid extraction machine platform 11. According to different requirements, the automatic control subsystem 10 may further comprise a first sensor S1 and a second sensor S2 disposed on the nucleic acid extraction machine platform 11, a third sensor S3 and a fourth sensor S4 disposed on the nucleic acid distribution machine platform 12, and a fifth sensor S5 disposed on the nucleic acid detection machine platform 13. According to different requirements, the automatic control subsystem 10 may further comprise a first transmission device T1 disposed between the nucleic acid extraction machine platform 11 and the nucleic acid distribution machine platform 12, and a second transmission device T2 disposed between the nucleic acid distribution machine platform 12 and the nucleic acid detection machine platform 13.

The computer device comprised in the automatic control subsystem 10 may basically comprise various processors, storages, and interfaces such as a flat cable, a communication interface, a network interface, and a man-machine interface or the like. The processors (e.g., central processing units, microprocessors, microcontrollers) may be programmed to interpret various instructions and execute various tasks or programs. The storages (e.g., memories, hard disks, optical disks, mobile disks) may be used to store various data required by the automatic control subsystem 10. The man-machine interfaces (e.g., graphical user interfaces) may assist the user in interacting with the automatic control subsystem 10.

The specimen placement area 112 may be arranged to accommodate a plurality of specimen containers. The specimen containers may be tubular containers (i.e., "specimen tube") or containers of other shapes for filling the specimen to be detected. The specimens may comprise, but are not limited to, blood specimens, urine specimens, upper respiratory tract mucus specimens, lower respiratory tract mucus specimens, sputum of lower respiratory tract, or the like. Relevant identification information of the specimen may be marked on the specimen container. For example, bar codes, QR codes, or other kinds of labels or information that can be used to identify relevant information of the specimen can be pasted outside the specimen container. In some embodiments, the specimen container may be a microcentrifuge tube with a screw cap, such as a 2 ml flat bottom screw cap microcentrifuge tube, which may seal the specimen in the specimen container through a cap (e.g., a screw cap). For another example, the specimen container may also be a 1.5 ml microcentrifuge tube, which is also called an eppendorf. In another preferred embodiment, the cap of the specimen container may also be a cap that can be pierced.

The specimen container operating device 113 may be configured to perform various automatic operations on the specimen container. In some embodiments, the specimen container operating device 113 may comprise a container holder 113a, a scanner 113b, a bottle cap separator 113c, a bottle cap detector 113d, etc. For example, after receiving the specimen container moved in by the robotic arm 111, the specimen container operating device 113 may fix the specimen container through the container holder 113a, and then confirm an identification of the specimen container through the scanner 113b (e.g., scan bar codes, QR codes, or other kinds of labels or data on the specimen container) to identify and record the relevant identification information of the specimen in the specimen container, which may include the information of the subject, the date of collection and the location of the specimen and the like. In some embodiments, the scanner 113b may scan in a fixed direction, and the container holder 113a may be rotated by a rotating device to rotate the specimen container so that the label attached to the specimen container is rotated to an angle where it can be scanned by the scanner 113b.

The container holder 113a may comprise a clip to clamp and fix the specimen container, or may comprise a groove structure to hold the specimen container after the specimen container is moved in by the robotic arm 111. After the specimen container is fixed by the container holder 113a, the specimen container together with the container holder 113a may be moved by a moving device to a position where the specimen container can be detected by the scanner 113b so that the scanner 113b can recognize the specimen container. In some embodiments, the specimen container together with the container holder 113a may be moved to a position where the bottom cap separator 113c can open the bottom cap to allow the bottom cap separator 113c to open the cap of the specimen container. In some embodiments, the specimen container together with the container holder 113a may also be moved to a position where the bottom cap separator 113c may open the cap and the scanner 113b may detect the specimen container.

When the identification of the specimen container is confirmed, the specimen container operating device 113 may open the cap of the specimen container by the bottle cap separator 113c. For example, when the specimen container is a microcentrifuge tube with a screw cap, the bottom cap separator 113c may comprise a cap clamping device and a rotating device. After the cap clamping device clamps the screw cap, the rotating device rotates the cap clamping device to open the screw cap of the specimen container.

In addition, the specimen container operating device 113 may confirm whether the screw cap of the specimen container is in an open state by the cap detector 113d. For example, the bottle cap detector 113d may comprise a movable element for touching the bottle opening of the specimen container, and determine whether the bottle cap of the specimen container is opened or not according to the touching result of the movable element with the bottle opening of the specimen container or measuring the width of the bottle opening.

The tip placement area 114 and the tip placement area 124 may have a lattice or hole-like structure to accommodate a plurality of unused tips, while the tip discard area 116 and the tip discard area 126 may be used to accommodate discarded tips.

The sample tray placement area 115 may be arranged to accommodate one or more sample trays P1, and all or part of the holes of the sample tray P1 placed in the sample tray placement area 115 are each filled with a specimen to be extracted. According to different embodiments, the sample tray P1 may be a 96-well tray (e.g., 8 horizontal rows by 12 vertical columns), a 192-well tray (e.g., 16 horizontal rows by 12 vertical columns), a 288-well tray (e.g., 16 horizontal rows by 18 vertical columns), or a 384-well tray (e.g., 16 horizontal rows by 24 vertical columns), but is not limited thereto.

The nucleic acid extraction device 117 may be any of various devices capable of extracting nucleic acids from various specimens. For example, the nucleic acid extraction device 117 may be an automatic magnetic bead operating platform, which uses a magnetic rod on a magnetic rod rack in the machine to move magnetic beads adsorbed with nucleic acids into different reagent tanks, and then uses a stirring sleeve sleeved on the outer layer of the magnetic rod to rapidly and repeatedly stir the liquid to result in uniform mixing, and finally obtains high-purity DNA or RNA nucleic acid molecules by cell lysis, nucleic acid adsorption, cleaning and elution.

The sample tray placement area 122 may be arranged to accommodate one or more sample trays P1, and all or part of the holes in the sample tray P1 placed in the sample tray placement area 122 are filled with samples (i.e., nucleic acids) extracted from the specimen by the nucleic acid extraction device 117. The size of the sample tray P1 placed in the sample tray placement area 122 may be the same as the size of the sample tray P1 placed in the sample tray placement area 115.

The first reagent placement area 123a may accommodate one or more first material trays P2a for accommodating first reagents required for distribution, and the first reagents may be various reactant, such as TaqMan™ Fast Virus 1-Step Master Mix and TaqMan™GTXpress™ Master Mix purchased from ThermoFisher. The second reagent placement area 123b may accommodate one or more second material trays P2b for accommodating second reagents, and the second reagents may be a stabilizer (in some embodiments, may also be a protective agent) (e.g., oil). The first reagent is mixed with primer pairs of a target gene locus in advance. When there is one target gene locus, the first reagent containing the first primer pair needs to be prepared in advance because the first primer pair containing the first forward primer and the first reverse primer of the first target gene locus is required. By analogy, if there are two target gene loci, then the first reagent containing the first primer pair and the first reagent containing the second primer pair individually need to be prepared in advance. After the nucleic acids and the first reagents are injected into holes of the detection tray P3, a second reagent may be subsequently injected to protect the nucleic acids and the first reagents in the holes.

The detection tray placement area 125 may be arranged to accommodate one or more detection trays P3 for nucleic acid distribution. Under different requirements, the detection tray placement area 133 may be arranged to accommodate one or more detection tray P3 to be detected, one or more detection tray P3 which have been detected, or both. The number of holes of the detection tray P3 is greater than the number of holes of the sample tray P1. For example, in the case where the sample tray P1 is a 96-well tray, the detection tray P3 may be a 192-well tray (e.g., 16 horizontal rows by 12 vertical columns), a 288-well tray (e.g., 16 horizontal rows by 18 vertical columns), a 384-well tray (e.g., 16 horizontal rows by 24 vertical columns), or a 480-well tray (e.g., 20 horizontal rows by 24 vertical columns), but is not limited thereto.

The nucleic acid detection device 132 may be any of various devices capable of detecting nucleic acids, such as an RT-PCR device that detects nucleic acid using Reverse Transcriptase Polymerase Chain Reaction (RT-PCR) technology. The technical principle of RT-PCR is to use the technology of Polymerase Chain Reaction (PCR) to amplify nucleic acid fragments (complementary DNA or DNA). If the nucleic acid fragments may be complementarily bonded with primer pairs, a signal of fluorescent protein will be generated. Therefore, whether there is a sequence of target genes in the nucleic acid may be determined by the signal quantity of fluorescent protein.

In some embodiments, the temperature of each of the specimen placement area 112 on the nucleic acid extraction machine platform 11, and the sample tray placement area 122, the detection tray placement area 125 and the first reagent placement area 123a on the nucleic acid distribution machine platform 12 may be maintained within a predetermined range (e.g., maintained at 3-5° C.).

The robotic arm 111, the robotic arm 121, and the robotic arm 131 may each be realized by various known mechanical structures, and not limited to arm types. By the control of the computer device comprised in the automatic control subsystem 10, the robotic arm 111, the robotic arm 121, and the robotic arm 131 are each capable of performing the following operations: moving in a plane or three-dimensional space; gripping or releasing a target object (e.g., a specimen container, a sample tray P1, a detection tray P3); inserting and taking or gripping a tip to suck in and spit out the target object (e.g., a specimen, a nucleic acid, a first reagent, a second reagent) by the tip; or other operations.

For example, the robotic arm 111 may use a tip to suck in a quantitative specimen from the specimen container, and move and spit it into one or more holes of the sample tray P1. The robotic arm 111 and the robotic arm 121 may insert and take or grip tips respectively from the tip placement area 114 and the tip placement area 124 to perform sucking in and spitting out of the specimen, the nucleic acid, the first reagent, and/or the second reagent, and respectively discard the used tip to the tip discard area 116 and the tip discard area 126. The robotic arm 111 and the robotic arm 121 may each comprise a ball-type rotating base and an actuating device, and the actuating device is disposed on the ball-type rotating base and rotate to any angle by the ball-type rotating base. The robotic arm 111 may move the sample tray P1 on the nucleic acid extraction machine platform 11 to the moving device T1, while the robotic arm 121 may move the sample tray P1 on the moving device T1 to the sample tray placement area 122 on the nucleic acid distribution machine platform 12, and move the detection tray P3 on the detection tray placement area 125 to the moving device T2. The robotic arm 131 may move the detection tray P3 on the moving device T2 into the detection tray placement area 133 or the nucleic acid detection device 132 on the nucleic acid detection machine platform 13. In some embodiments, the robotic arm 131 may comprise a moving rail and an actuating device suspended on the moving rail. The actuating device may move horizontally on the two-dimensional moving rail and vertically at any certain point on the two-dimensional moving rail. In addition, the robotic arm 131 may touch the display interface of the nucleic acid detection device 132 to control the operation of the nucleic acid detection device 132.

The first sensor S1, the second sensor S2, the third sensor S3, the fourth sensor S4, and the fifth sensor S5 are devices that may sense whether a target object appears in a certain space by light, sound waves, or various other sensing mechanisms. Taking the first sensor S1 as an example, the first sensor S1 may be configured to sense whether the robotic arm 111 indeed obtains unused tips from the tip placement area 114. After the robotic arm 111 tries to grip a tip from the tip placement area 114, the robotic arm 111 may move to a space where the first sensor S1 can sense the tip. If the first sensor S1 sense the tip, it confirms that the robotic arm 111 indeed grips the tip. In some embodiments, only as the first sensor S1 confirms that the robotic arm 111 indeed grips the tip, will the robotic arm 111 move to the specimen container operating device 113 and suck the specimen in the specimen container by the tip. By the sensing functions of the first sensor S1, the second sensor S2, the third sensor S3, the fourth sensor S4, and the fifth sensor S5, the automatic control subsystem 10 may monitor whether the automatic operations of the automatic nucleic acid detection system 1 are correct (described in detail later).

The first transmission device T1 and the second transmission device T2 are devices with transmission functions (e.g., transmission belts, transmission vehicles) for transmitting target objects. For example, the automatic control subsystem 10 may transmit the sample tray P1 from the nucleic acid extraction machine platform 11 to the nucleic acid distribution machine platform 12 by the first transmission device T1, and may transmit the detection tray P3 from the nucleic acid distribution machine platform 12 to the nucleic acid detection machine platform 13 by the second transmission device T2.

In some embodiments, it may be unnecessary to provide the first transmission device T1 and the second transmission device T2, and instead, the robotic arm 111, the robotic arm 121, and/or the robotic arm 131 by themselves transmit the sample tray P1 from the nucleic acid extraction machine platform 11 to the nucleic acid distribution machine platform 12, and transmit the detection tray P3 from the nucleic acid distribution machine platform 12 to the nucleic acid detection machine platform 13. In some embodiments, the automatic control subsystem 10 may not need to move the sample tray P1 and/or the detection tray P3 by a specific design.

It shall be appreciated that, the configuration (e.g., number, shape, size, location) of each element (e.g., each system, machine platform, or device) depicted in FIG. 2 is only an example. The configuration may be adjusted by a person having ordinary skill in the art according to different requirements in the case where it can be implemented. In addition, the space separation or relative positions of the nucleic acid extraction machine platform 11, the nucleic acid distribution machine platform 12, the nucleic acid detection machine platform 13 and the automatic control subsystem 10 depicted in FIG. 2 are not limited. In some embodiments, the spatial regions of the nucleic acid extraction machine platform 11, the nucleic acid distribution machine platform 12, and the nucleic acid detection machine platform 13 may overlap. For example, in the case where it can be implemented, the nucleic acid extraction machine platform 11 and the nucleic acid distribution machine platform 12 may share a same robotic arm provided by the automatic control subsystem 10, and the robotic arm may perform all or part of operations on the nucleic acid extraction machine platform 11 and the nucleic acid distribution machine platform 12.

Figure 3A:
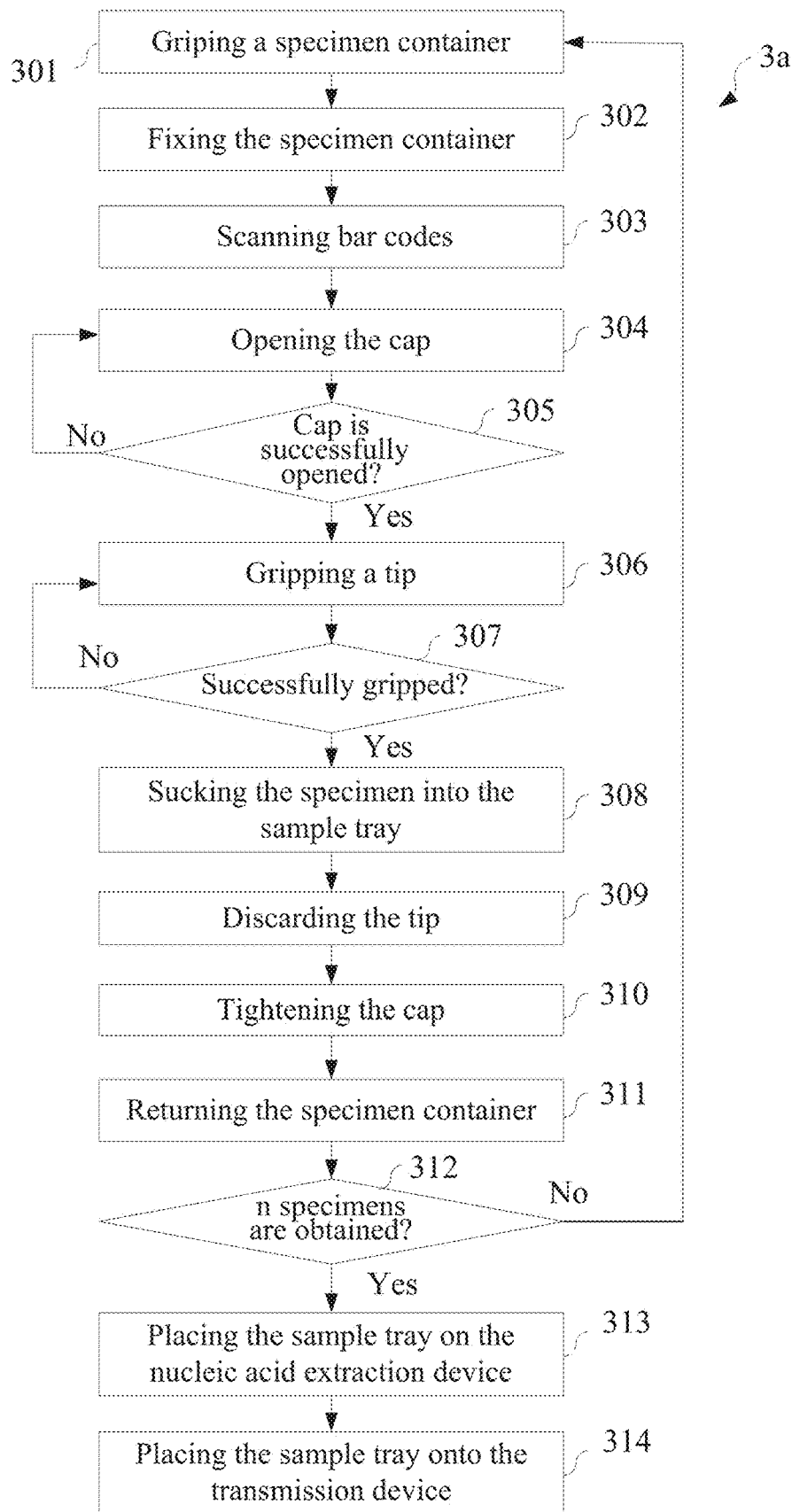
FIG. 3A to FIG. 3C illustrate schematic views of the operation of the automatic nucleic acid detection system described in FIG. 2.
Figure 3B:
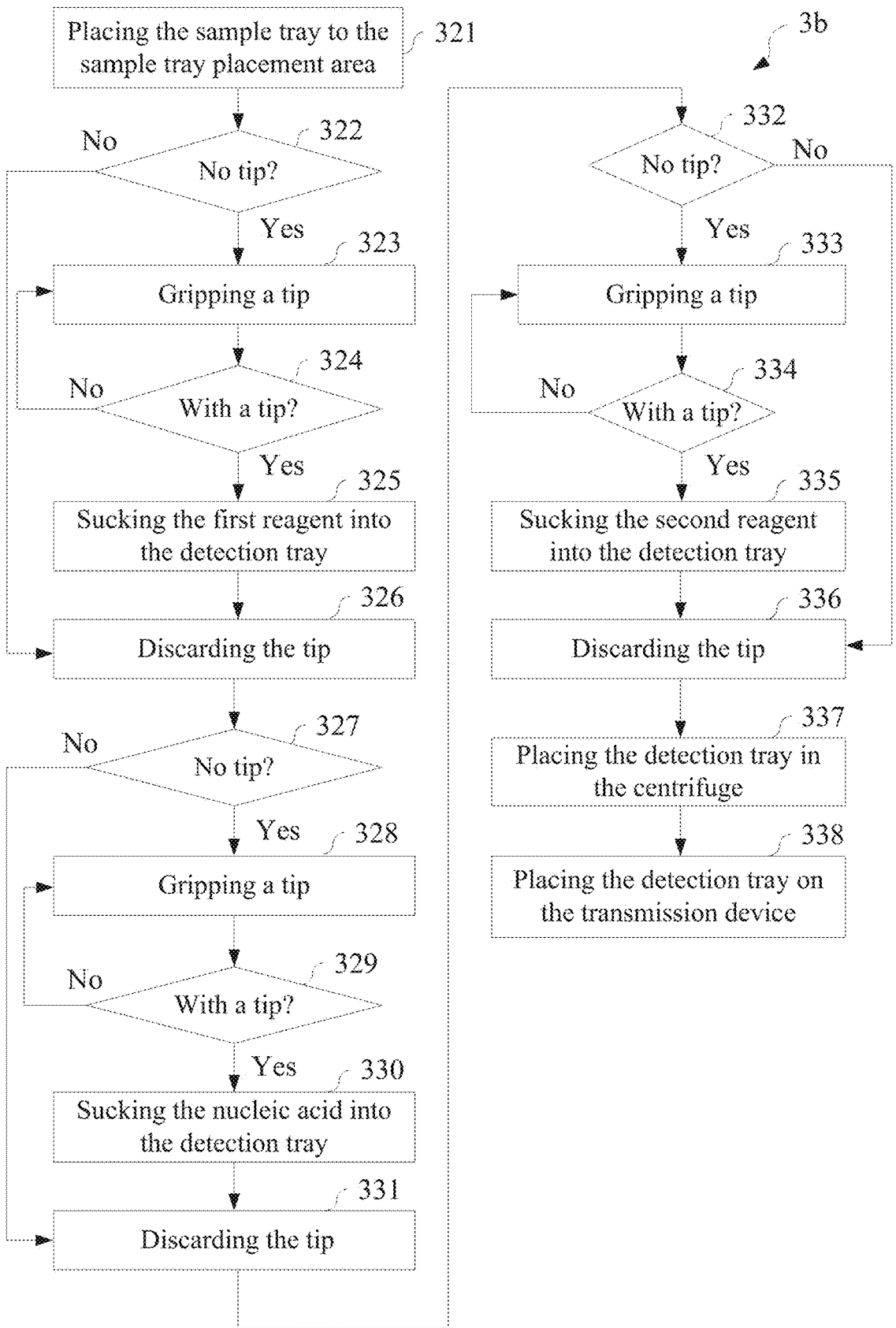
Figure 3C:
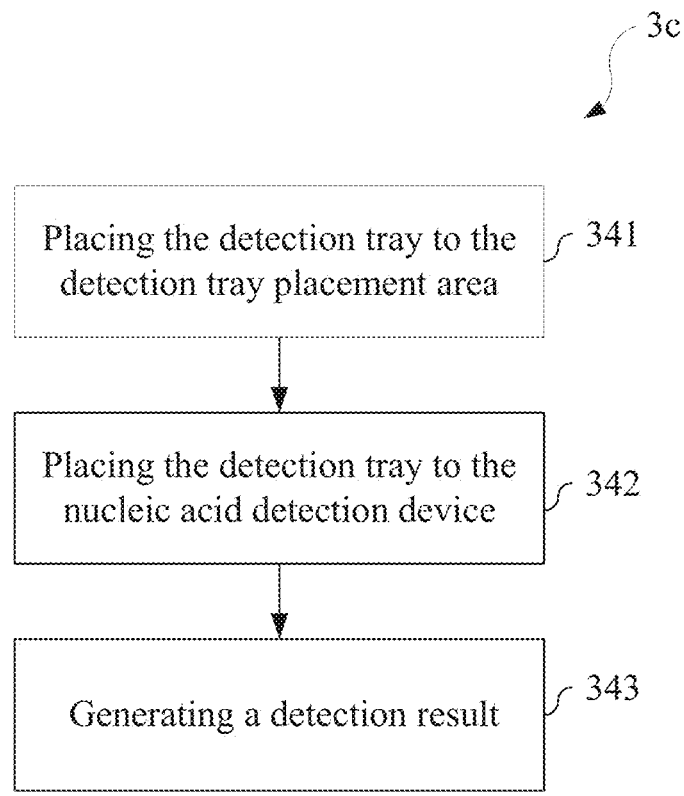

Next, the operation details of the automatic nucleic acid detection system 1 will be explained through FIG. 3A to FIG. 3C. FIG. 3A illustrates an operation process 3A of the automatic nucleic acid detection system 1 on the nucleic acid extraction machine platform 11 according to some embodiments of the present invention, FIG. 3B illustrates an operation process 3b of the automatic nucleic acid detection system 1 on the nucleic acid distribution machine platform 12 according to some embodiments of the present invention, and FIG. 3C illustrates an operation process 3c of the automatic nucleic acid detection system 1 on the nucleic acid detection machine platform 13 according to some embodiments of the present invention.

Referring to FIG. 3A, in the process 3a, the robotic arm 111 first grips a specimen container from the specimen placement area 112 (labeled as action 301), and then moves the specimen container into the specimen container operating device 113 so that the specimen container operating device 113 fixes the specimen container (labeled as action 302), and scans and registers information of the specimen container (labeled as action 303) (i.e., confirms an identification of the specimen container). Depending on different applications, actions 304 and 305 may be optionally performed after action 303 is completed (i.e., when the identification of the specimen container is confirmed). In detail, in the case where the specimen container is provided with a cap, the specimen container operating device 113 may open the cap of the specimen container (labeled as action 304) after completing the action 303, and may optionally confirm whether the cap of the specimen container has been successfully opened (labeled as action 305) by the bottom cap detector 113d. It will enter action 306 after the cap of the specimen container has been successfully opened. In a preferred embodiment, when the specimen container has a cap that can be pierced, it may be unnecessary to perform the actions 304 and 305 after the action 303 is completed. Instead, the action 306 is directly performed following action 303, and then a pipette may be configured by the robotic arm 111 to penetrate through the cap of the specimen container to directly suck the specimen inside.

Next, in the action 306, the robotic arm 111 moves to the tip placement area 114 to insert and take or grip the tip. In some cases, optionally, the first sensor S1 may confirm whether the robotic arm 111 indeed grips the tip (labeled as action 307) between the action 306 and the action 308. If the confirmation result is "Yes", then the robotic arm 111 uses the tip to suck the specimen in the specimen container and spit the specimen into the corresponding hole of the sample tray P1 (i.e., performs action 308). Otherwise, the robotic arm 111 may try to grip the tip again, and performs the action 308 only after the tip is indeed gripped. The robotic arm 111 may discard the tip to the tip discard area 116 (labeled as action 309) after spitting the specimen into the sample tray P1 of the sample tray placement area 115 using the tip. After the robotic arm 111 discards the tip, the specimen container operating device 113 may close the cap of the specimen container (e.g., tighten the screw cap of the specimen container by a rotating device) (labeled as action 310). When the specimen container has a cap that can be pierced, the action 310 may also be omitted. Next, the robotic arm 111 grips the specimen container and place the specimen container back to the specimen placement area 112 (labeled as action 311). In some embodiments, the robotic arm 111 may discard the specimen container instead of placing the specimen container back to the specimen placement area 112.

The above actions 301 to 311 are actions performed by the robotic arm 111 for one specimen container. The robotic arm 111 may perform these actions for each different specimen. By the practice where scanning and registering the information of the specimen, opening the cap, sucking and spitting the specimen into the sample tray P1 are performed sequentially on only one specimen container at a time, it can be ensured that each piece of information registered for the specimen is consistent with the specimen filled into the sample tray P1, and thus information registration errors are avoided.

In some embodiments, the robotic arm 111 may also perform the actions 301 to 311 simultaneously for a plurality of specimen containers (for example, a row or a group of specimen containers). For example, in the action 301, the robotic arm 111 may simultaneously grip a row of specimen containers and move the row of specimen containers to the specimen container operating device 113. In the action 302, the specimen container operating device 113 may fix the row of specimen containers at the same time. In the action 303, the specimen container operating device 113 may scan and register the information of the entire row of specimen containers at the same time. The other actions can be perform in a similar way. In this case, efficiency may be additionally improved while ensuring that each group of information registered for the group of specimens matches the group of specimens filled into the sample tray P1 and avoiding information registration error.

It will be determined that whether the robotic arm 111 has performed the actions 301 to 311 once for each of the specimens that need to be detected (labeled as action 312); in other words, it will be determined that whether the number of times each set of actions 301 to 311 have been performed has reached a preset number (i.e., whether a preset number of specimens (e.g., n specimens) have been sucked and spitted into the sample tray P1). As it is determined that the robotic arm 111 has performed the actions 301 to 311 once for each of the specimens that need to be detected, the robotic arm 111 may place the sample tray P1 on the nucleic acid extraction device 117 (labeled as action 313), and the nucleic acid extraction device 117 extracts the nucleic acid from each specimen in the sample tray P1 to generate a sample tray P1 containing a specific amount of nucleic acids. Then, the robotic arm 111 places the sample tray P1 containing the specific amount of nucleic acids onto the first transmission device T1 (labeled as action 314), and the first transmission device T1 transmits the sample tray P1 to the nucleic acid distribution machine platform 12 to complete the process 3a.

In some embodiments, the second sensor S2 may be used to confirm whether the sample tray P1 is indeed placed on the nucleic acid extraction device 117 after the action 313. In this case, the nucleic acid extraction device 117 performs nucleic acid extraction on the specimens in the sample tray P1 only when the sensor S2 senses that the sample tray is indeed placed on the nucleic acid extraction device 117.

Next, referring to FIG. 3B, when the process 3a is completed, the system may enter the process 3b. In the process 3b, the robotic arm 121 may first move the sample tray P1 on the first transmission device T1 to the sample tray placement area 122 (labeled as action 321). In some embodiments, before performing the action 321, the third sensor S3 may be used to confirm whether the first transmission device T1 indeed moves the sample tray P1 to the area of the nucleic acid distribution machine platform 12, and the action 321 is performed only when the third sensor S3 senses the presence of the sample tray P1 in the area of the nucleic acid distribution machine platform 12.

After the action 321, if the first reagent required for the distribution has been placed in the first reagent placement area 123a and the second reagent has also been placed in the second reagent placement area 123b, then the robotic arm 121 may perform the following actions in sequence: inserting and taking or griping a new tip from the tip placement area 124 (labeled as action 323), sucking the first reagent into the corresponding hole of the detection tray P3 (labeled as action 325), discarding the tip (labeled as action 326), inserting and taking or griping a new tip from the tip placement area 124 (labeled as action 328), sucking the nucleic acid from the sample tray P1 and spitting it into the corresponding hole of the detection tray P3 (labeled as action 330), discarding the tip (labeled as action 331), inserting and taking or griping a new tip from the tip placement area 124 (labeled as action 333), sucking the second reagent into the corresponding hole of the detection tray P3 (labeled as action 335), and discarding the tip (labeled as action 336).

After a nucleic acid and corresponding first reagent are injected into a hole of the detection tray P3 (i.e., after the action 330), the nucleic acid and the first reagent in the hole may be protected by injecting a second reagent into the hole. However, according to different applications, in some other embodiments, the second reagent may also not be used (i.e., actions 333 and 335 may be omitted). Instead, the hole containing the nucleic acid and the first reagent in the detection tray P3 may be sealed in other ways (e.g., covering with a cap, a film, or a sticker).

Optionally, each time before the robotic arm 121 is to insert and take or grip a tip (i.e., each time before the actions 323, 328 and 333 are performed), the fourth sensor S4 may be used to confirm whether the robotic arm 121 has not inserted and taken or gripped any tip (labeled as actions 322, 327 and 332, respectively). If the confirmation result is "Yes", then the robotic arm 121 moves to the tip placement area 124 to insert and take or grip the tip (i.e., performs the actions 323, 328 and 333), and if the confirmation result is "No", then the robotic arm 121 moves the tip to the tip discard area 126. In addition, optionally, each time after the robotic arm 121 completes the inserting and taking or the gripping of the tip (i.e., each time after the actions 323, 328 and 333 are performed), the fourth sensor S4 may also be used to confirm whether the robotic arm 121 has successfully inserted and taken or gripped the tip (labeled as actions 324, 329 and 334, respectively). If the confirmation result is "Yes", then the robotic arm 121 sucks the nucleic acid/first reagent/second reagent into the detection tray (i.e., performs action 325/action 330/action 335); and if the confirmation result is "No", then the robotic arm 121 may move to the tip placement area 124 again to insert and take or grip a tip (i.e., performs the actions 323, 328, 333).

Optionally, each time after the robotic arm 121 do an action of discarding the tip (i.e., each time after the actions 326, 331 and 336 are performed), the fourth sensor S4 may also be used to confirm whether the robotic arm 121 indeed discards the tip no matter the robotic arm 121 will again insert and take or grip any tip or not.

By the above operations of the fourth sensor S4, the automatic control subsystem 10 will be able to monitor whether the nucleic acid in each hole in the sample tray P1, the corresponding first reagent in the first material tray P2a, and the corresponding second reagent in the second material tray P2b are all successfully distributed into the holes in the detection tray P3 during the nucleic acid distribution process.

When a plurality of gene loci are required, the automatic control subsystem 10 may distribute the nucleic acid in the sample tray P1, the first reagent in the first material tray P2a, and the second reagent in the second material tray P2b into a plurality of holes of the detection tray P3 for multiple times. In the case where the robotic arm 121 sucks only one nucleic acid/one first reagent/one second reagent at a time, a gene locus corresponding to a certain specimen will be generated each time the above actions 323, 325, 326, 328, 330, 331, 333, 335 and 336 are performed. However, in the case where the robotic arm 121 sucks a plurality of nucleic acids/a plurality of first reagents/a plurality of second reagents at a time, a plurality of gene loci corresponding to a plurality of specimens respectively may be generated each time the above actions 323, 325, 326, 328, 330, 331, 333, 335 and 336 are performed.

In some embodiments, the robotic arm 121 may insert and take or grip a plurality of tips at a time by a multi-claw pipette, and simultaneously suck the first reagents, the nucleic acids, or the second reagents in a plurality of holes (e.g., a row of holes) into a plurality of corresponding holes (e.g., a row of holes) in the detection tray P3 by the plurality of tips. For example, in the case where the sample tray P1 is a 96-well tray (e.g., 8 horizontal rows by 12 vertical columns), the robotic arm 121 may use an eight-claw pipette to take eight tips at a time and suck in or spit out eight nucleic acids at a time (e.g., a certain vertical column of the 96-well sample tray). Similarly, in the case where the first reagents are placed in a 96-well first material tray P2a and the second reagents are placed in a 96-well second material tray P2b, the robotic arm 121 may use an eight-claw pipette to take eight tips at a time and suck in or spit out eight first reagents or eight second reagents at a time (e.g., a certain vertical column of the 96-well first material tray P2a or the 96-well second material tray P2b).

Figure 4:
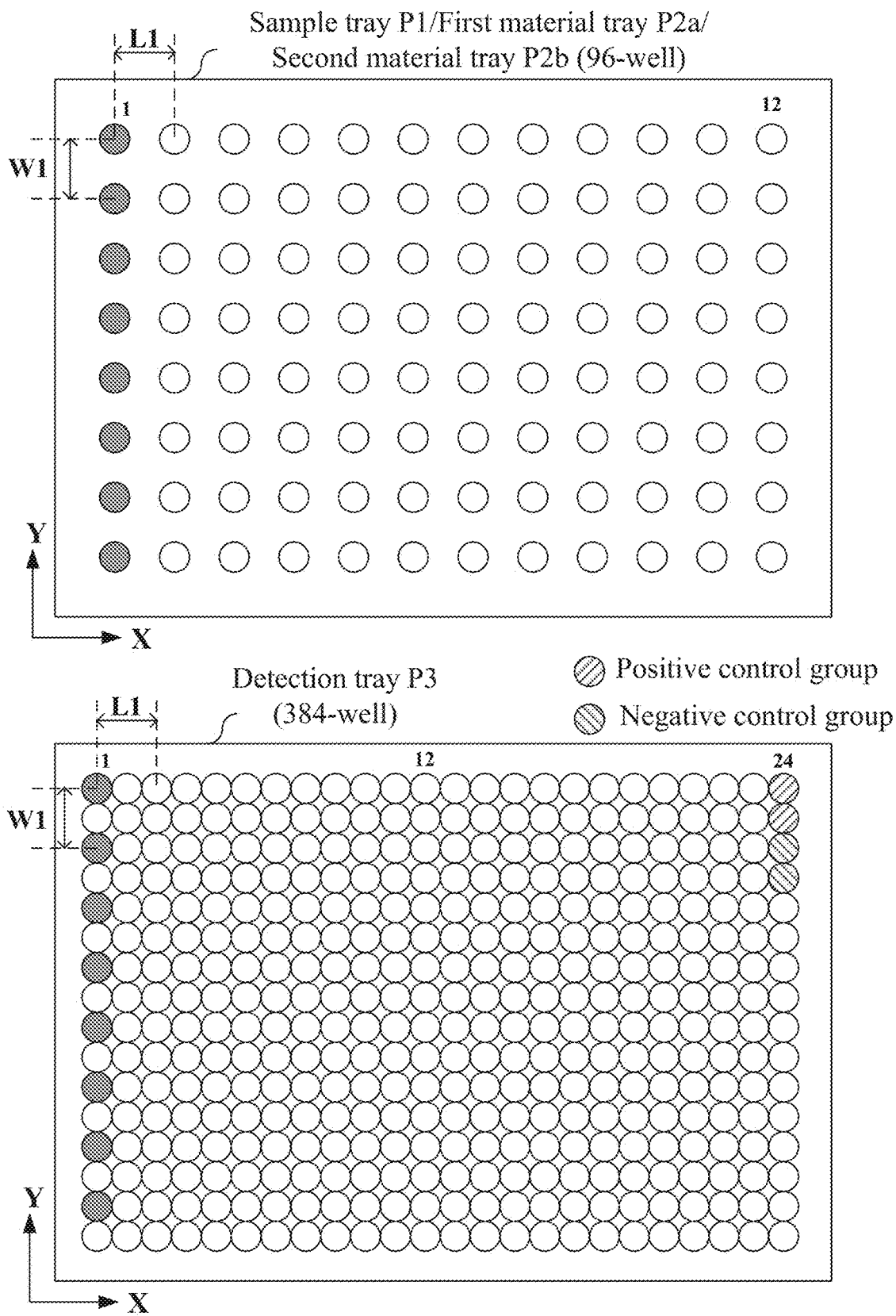
FIG. 4 is a schematic view of nucleic acid distribution according to some embodiments of the present invention.

FIG. 4 is a schematic view of nucleic acid distribution according to some embodiments of the present invention. Referring to FIG. 4, the size (area) of the detection tray P3 (384-well tray) is the same as that of the sample tray P1 (96-well tray), the first material tray P2a (96-well tray), and the second material tray P2b (96-well tray), and the spacing "W1" between two adjacent holes (gray parts) in any vertical column of the sample tray P1/the first material tray P2a/the second material tray P2b is equal to the spacing "W1" between two holes (gray parts) that are spaced apart by one hole in any vertical column of the detection tray P3. In addition, the spacing "L1" between two adjacent holes in any horizontal row of the sample tray P1/the first material tray P2a/the second material tray P2b is equal to the spacing "L1" between two holes spaced apart by one hole in any horizontal row of the detection tray P3. That is, in this exemplary example, the number of holes of the detection tray P3 is four times the number of holes of the sample tray P1/the first material tray P2a/the second material tray P2b.

In the case where the interval between tips gripped by the multi-claw pipette (e.g., an eight-claw pipette, a 12-claw pipette, or a 16-claw pipette) used by the robotic arm 121 is also equal to "W1", the robotic arm 121 may simultaneously suck a plurality of nucleic acids/first reagents/second reagents from the holes (gray parts) in the first vertical column of the sample tray P1/the first material tray P2a/the second material tray P2b, and then simultaneously spit them into the odd-numbered holes (gray parts) in the first vertical column of the detection tray P3. Then, the plurality of nucleic acids/first reagents/second reagents may be simultaneously spitted into the even-numbered holes (white parts) in the first vertical column of the detection tray P3 again simply by moving the robotic arm 121 with a distance of "W1/2" in the direction of the "−Y" axis. By the above means, a plurality of gene loci required for testing a plurality of specimens may be easily generated.

For another example, the robotic arm 121 may also simultaneously suck a plurality of nucleic acids/first reagents/second reagents from the holes (gray parts) in the first vertical column of the sample tray P1/the first material tray P2a/the second material tray P2b, and then simultaneously spit them into the odd-numbered holes (gray parts) in the first vertical column of the detection tray P3. Then, the robotic arm 121 may be moved by a distance of "L1/2" in the direction of the "X axis," and then simultaneously spit the plurality of nucleic acids/first reagents/second reagents into the odd-numbered holes in the second vertical column of the detection tray P3 again. By the above means, a plurality of gene loci required for testing a plurality of specimens may also be easily generated.

In some embodiments, in addition to the above-mentioned distribution method, the robotic arm 121 may also simultaneously distribute the plurality of nucleic acids in the sample tray P1, the plurality of first reagents in the first material tray P2a, and the plurality of second reagents in the second material tray P2b into a plurality of corresponding holes of the detection tray P3 for multiple times according to other preset rules.

In FIG. 4, some holes of the detection tray P3 (384-well tray) may be used as experimental control groups (i.e., a positive control group and a negative control group). The experimental control groups may be arranged in the same vertical column of the detection tray P3. One gene locus requires a positive control group and a negative control group, while two gene loci requires two positive control groups and two negative control groups, and so on.

According to different requirements or applications, a plurality of gene loci required for testing a certain specimen may be filled with the same sample (nucleic acid), but filled with different first reagents (i.e., having different reaction materials but with the same substrate). In some practical applications of virus detection, for example, the detection of the virus can be confirmed only if the detection results at two gene loci are all positive.

Next, referring back to FIG. 3B, after all the nucleic acids, the first reagents, and the second reagents have been distributed to the detection tray P3, the robotic arm 121 may place the detection tray P3 in the centrifuge 127 (labeled as action 337). In the action 337, the centrifuge 127 may generate a centrifugal force to settle and mix the nucleic acid and the first reagent in each hole in the detection tray P3. When the volume of the nucleic acid in each hole of the detection tray P3 is less than a preset value (e.g., less than or equal to 10 µl), the nucleic acid and the first reagent in each hole in the detection tray P3 may be effectively mixed only by the centrifugal force generated by the centrifuge 127. In other words, in this case, the nucleic acid and the first reagent can be effectively mixed without sucking and spitting the nucleic acid and the first reagent for multiple times by the robotic arm 121 or oscillating by the oscillator. In some embodiments, the nucleic acid and the first reagent may be effectively mixed when the centrifuge 127 is operated at a rotation speed of 1500 to 4500 rpm for 5 to 30 seconds.

Since the optical reaction of the hole containing the nucleic acid, the first reagent and the second reagent is different from that of the hole not containing the nucleic acid, the first reagent and the second reagent, the automatic control subsystem 10 may further comprise an optical detector (not shown) in some embodiments, and monitor whether each hole in the detection tray P3 contains the nucleic acid, the first reagent and the second reagent by the optical detection function provided by the optical detector. For example, the optical detector may comprise a charge coupled device (CCD). In this case, the automatic control subsystem 10 performs the action 337 only when it is confirmed that each hole in the detection tray P3 contains the nucleic acid, the first reagent, and the second reagent.

After the action 337, the robotic arm 121 may place the detection tray P3 on the second transmission device T2 (labeled as action 338), and then the second transmission device T2 transmits the detection tray P3 to the nucleic acid detection machine platform 13 to complete the process 3b.

Next, referring to FIG. 3C, when the process 3b is completed, the system may enter the process 3c. In the process 3c, first the robotic arm 131 may move the detection tray P3 from the second transmission device T2 to the detection tray placement area 133 (labeled as action 341). In some embodiments, optionally, the fifth sensor S5 may be used to confirm whether the second transmission device T2 indeed moves the detection tray P3 to the area of the nucleic acid detection machine platform 13 before the action 341, and the action 341 is performed only when the fifth sensor S5 senses the presence of the detection tray P3 in the area of the nucleic acid detection machine platform 13.

After the action 341, if the nucleic acid detection device 132 is ready, the robotic arm 131 may move the detection tray P3 placed in the detection tray placement area 133 into the nucleic acid detection device 132 (labeled as action 342), and then the nucleic acid detection device 132 detects the detection tray P3 and generates a detection result (labeled as action 343) to complete the process 3c. Alternatively, when the second transmission device T2 moves the detection tray P3 to the area of the nucleic acid detection machine platform 13, the robotic arm 131 may also omit the action 341 and directly perform the action 342 if the nucleic acid detection device 132 is ready. The detection results generated by the nucleic acid detection device 132 may be stored in the computer device comprised in the automatic control subsystem 10 and transmitted to other external devices by the computer device.

FIG. 5 is a schematic view of an automatic nucleic acid detection method according to some embodiments of the present invention. The content shown in FIG. 5 is only for the purpose of illustrating embodiments of the present invention, and is not intended to limit the scope claimed in the present invention.

Referring to FIG. 5, the automatic nucleic acid detection method 5 may comprise the following steps: performing, by an automatic control subsystem, on a nucleic acid extraction machine platform, nucleic acid extraction on one or a plurality of specimens in a sample tray to generate one or a plurality of corresponding nucleic acids in the sample tray (labeled as step 501); distributing, by the automatic control subsystem, on a nucleic acid distribution machine platform, the nucleic acid in each hole of the sample tray and a first reagent into a plurality of holes of a detection tray, wherein the number of holes of the detection tray is greater than the number of holes of the sample tray (labeled as step 502); and performing, by the automatic control subsystem, on a nucleic acid detection machine platform, nucleic acid detection on the detection tray (labeled as step 503).

In some embodiments, the size of the sample tray is the same as that of the detection tray.

In some embodiments, in the step 502, the automatic control subsystem correspondingly distributes a plurality of nucleic acids in a plurality of holes in the sample tray into a plurality of holes in the detection tray simultaneously for multiple times.

In some embodiments, in addition to the steps 501 to 503, the automatic nucleic acid detection method 5 further comprises the following step: monitoring, by the automatic control subsystem, whether the nucleic acid in each hole of the sample tray and the first reagent have been successfully distributed into a plurality of holes in the detection tray.

In some embodiments, in addition to the steps 501 to 503, the automatic nucleic acid detection method 5 further comprises the following steps: confirming, by the automatic control subsystem, an identification of a specimen container, wherein the specimen container contains the specimen or one of the plurality of specimens; and placing, by the automatic control subsystem, the specimen in the specimen container in the sample tray when the identification of the specimen container is confirmed.

In some embodiments, in addition to the steps 501 to 503, the automatic nucleic acid detection method 5 further comprises the following steps: confirming, by the automatic control subsystem, an identification of a specimen container, wherein the specimen container contains the specimen or one of the plurality of specimens; opening a cap of the specimen container by the automatic control subsystem; and placing, by the automatic control subsystem, the specimen in the specimen container in the sample tray when the identification of the specimen container is confirmed.

In some embodiments, in addition to the steps 501 to 503, the automatic nucleic acid detection method 5 further comprises the following steps: confirming, by the automatic control subsystem, an identification of a specimen container, wherein the specimen container contains the specimen or one of the plurality of specimens; opening, by the automatic control subsystem, a cap of the specimen container; monitoring, by the automatic control subsystem, whether the cap of the specimen container has been successfully opened; and placing, by the automatic control subsystem, the specimen in the specimen container in the sample tray when the identification of the specimen container is confirmed.

In some embodiments, in addition to the steps 501 to 503, the automatic nucleic acid detection method 5 further comprises the following step: mixing, by the automatic control subsystem, on the nucleic acid distribution machine platform, the nucleic acid and the first reagent in each hole in the detection tray in a centrifugal manner.

In some embodiments, in addition to the steps 501 to 503, the automatic nucleic acid detection method 5 further comprises the following step: mixing, by the automatic control subsystem, on the nucleic acid distribution machine platform, the nucleic acid and the first reagent in each hole in the detection tray in a centrifugal manner. When the volume of the nucleic acid in each hole in the detection tray is less than a preset value, the automatic control subsystem mixes the nucleic acid and the first reagent in each hole in the detection tray only in the centrifugal manner.

In some embodiments, in addition to the steps 501 to 503, the automatic nucleic acid detection method 5 further comprises the following steps: adding, by the automatic control subsystem, a second reagent into each hole in the detection tray that contains the nucleic acid and the first reagent; and monitoring, by the automatic control subsystem, whether each hole in the detection tray is successfully added with the nucleic acid, the first reagent, and the second reagent.

In some embodiments, in addition to the steps 501 to 503, the automatic nucleic acid detection method 5 further comprises the following step: sealing, by the automatic control subsystem, each hole in the detection tray that contains the nucleic acid and the first reagent.

In some embodiments, in addition to the steps 501 to 503, the automatic nucleic acid detection method 5 further comprises the following step: monitoring, by the automatic control subsystem, whether each hole in the detection tray contains the nucleic acid and the first reagent in an optical manner.

In some embodiments, the temperature of each of a specimen placement area on the nucleic acid extraction machine platform, a detection tray placement area and a first reagent placement area on the nucleic acid distribution machine platform is maintained within a preset range.

Each embodiment of the automatic nucleic acid detection method 5 essentially corresponds to a certain embodiment of the automatic nucleic acid detection system 1. Therefore, even if not described in detail above for each embodiment of the automatic nucleic acid detection method 5, a person having ordinary skill in the art may directly appreciate the embodiments of the automatic nucleic acid detection method 5 that are not described in detail according to the above description for the automatic nucleic acid detection system 1.

Figure 6:
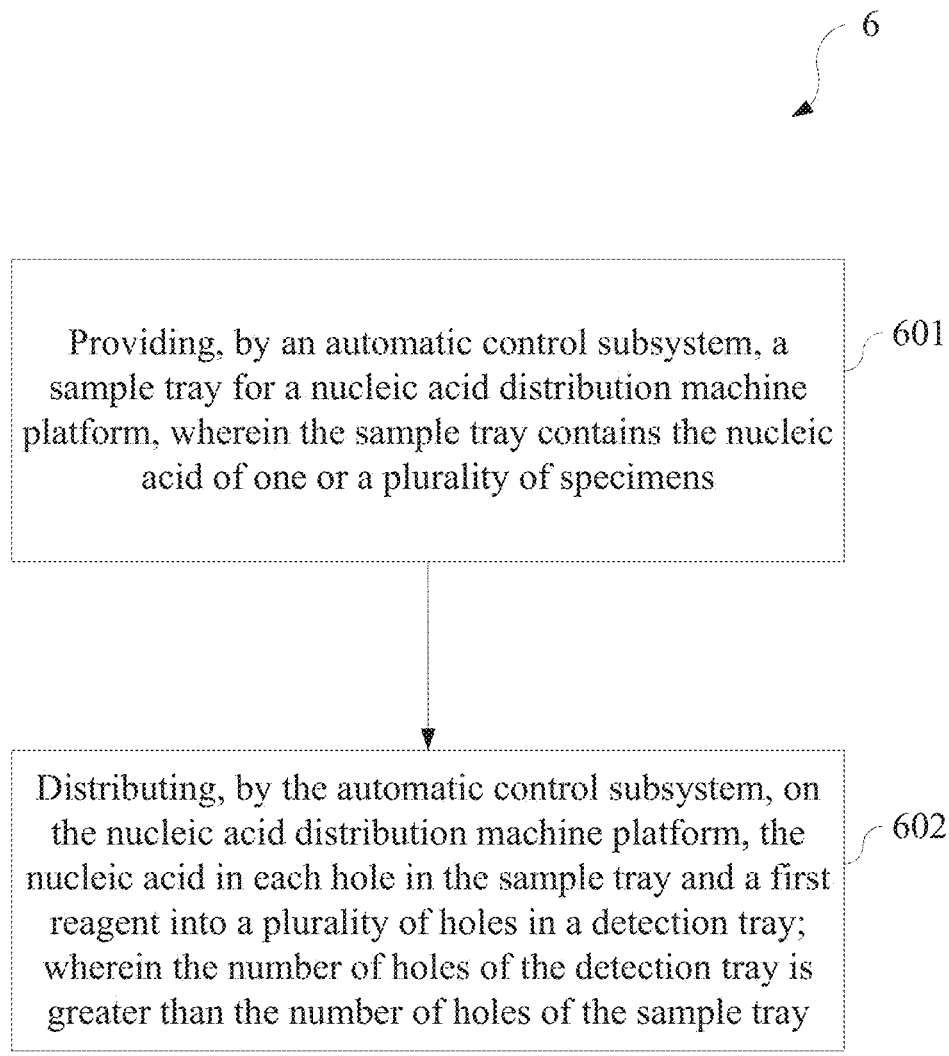
FIG. 6 is a schematic view of an automatic nucleic acid distribution method according to some embodiments of the present invention.

FIG. 6 is a schematic view of an automatic nucleic acid distribution method according to some embodiments of the present invention. The content shown in FIG. 6 is only for the purpose of illustrating embodiments of the present invention, and is not intended to limit the scope claimed in the present invention.

Referring to FIG. 6, an automatic nucleic acid distribution method 6 may comprise the following steps: providing, by an automatic control subsystem, a sample tray for a nucleic acid distribution machine platform, wherein the sample tray contains the nucleic acid of one or a plurality of specimens (labeled as step 601); and distributing, by the automatic control subsystem, on the nucleic acid distribution machine platform, the nucleic acid in each hole in the sample tray and a first reagent into a plurality of holes in a detection tray; wherein the number of holes of the detection tray is greater than the number of holes of the sample tray (labeled as step 602).

In some embodiments, the size of the sample tray is the same as that of the detection tray.

In some embodiments, in the step 602, the automatic control subsystem correspondingly distributes a plurality of nucleic acids in a plurality of holes in the sample tray into a plurality of holes in the detection tray simultaneously for multiple times.

In some embodiments, in addition to the steps 601 to 602, the automatic nucleic acid distribution method 6 may further comprise the following step: monitoring, by the automatic control subsystem, whether the nucleic acid in each hole of the sample tray and the first reagent have been successfully distributed into a plurality of holes in the detection tray.

In some embodiments, in addition to the steps 601 to 602, the automatic nucleic acid distribution method 6 may further comprise the following step: mixing, by the automatic control subsystem, the nucleic acid and the first reagent in each hole in the detection tray in a centrifugal manner on the nucleic acid distribution machine platform.

In some embodiments, in addition to the steps 601 to 602, the automatic nucleic acid distribution method 6 may further comprise the following step: mixing, by the automatic control subsystem, the nucleic acid and the first reagent in each hole in the detection tray in a centrifugal manner on the nucleic acid distribution machine platform. When the volume of the nucleic acid in each hole in the detection tray is less than a preset value, the automatic control subsystem mixes the nucleic acid and the first reagent in each hole in the detection tray only in the centrifugal manner.

In some embodiments, in addition to the steps 601 to 602, the automatic nucleic acid distribution method 6 further comprises the following steps: adding, by the automatic control subsystem, a second reagent into each hole in the detection tray that contains the nucleic acid and the first reagent; and monitoring, by the automatic control subsystem, whether each hole in the detection tray is successfully added with the nucleic acid, the first reagent, and the second reagent.

In some embodiments, in addition to the steps 601 to 602, the automatic nucleic acid distribution method 6 may further comprise the following step: sealing, by the automatic control subsystem, each hole in the detection tray that contains the nucleic acid and the first reagent.

In some embodiments, in addition to the steps 601 to 602, the automatic nucleic acid distribution method 6 may further comprise the following step: monitoring, by the automatic control subsystem, whether each hole in the detection tray contains the nucleic acid and the first reagent in an optical manner.

Each embodiment of the automatic nucleic acid distribution method 6 essentially corresponds to a certain embodiment of the automatic nucleic acid detection system 1.

Therefore, even if not described in detail above for each embodiment of the automatic nucleic acid distribution method 6, a person having ordinary skill in the art may directly appreciate the embodiments of the automatic nucleic acid distribution method 6 that are not described in detail according to the above description for the automatic nucleic acid detection system 1.

The above disclosure provides the detailed technical contents and inventive features thereof for some embodiments of the present invention. A person having ordinary skill in the art may proceed with a variety of modifications and replacements based on the disclosures and suggestions of the invention as described without departing from the characteristics thereof. Nevertheless, although such modifications and replacements are not fully disclosed in the above descriptions, they have substantially been covered in the following claims as appended.

What is claimed is:

1. An automatic nucleic acid detection system, comprising:
    a nucleic acid extraction machine platform, wherein a nucleic acid extraction device is disposed on the nucleic acid extraction machine platform;
    a nucleic acid distribution machine platform, wherein a second robotic arm is disposed on the nucleic acid distribution machine platform;
    a nucleic acid detection machine platform, wherein a nucleic acid detection device is disposed on the nucleic acid detection machine platform; and
    an automatic control subsystem, comprising a computer device and the second robotic arm and being connected with the nucleic acid extraction machine platform, the nucleic acid distribution machine platform and the nucleic acid detection machine platform,
    wherein the nucleic acid extraction device is configured to perform, on the nucleic acid extraction machine platform, nucleic acid extraction on one or a plurality of specimens in a sample tray to generate one or a plurality of corresponding nucleic acids in the sample tray;
    wherein the computer device is configured to control the second robotic arm to perform, on the nucleic acid distribution machine platform, nucleic acid distribution from one sample tray having a fewer number of holes to one detection tray having a greater number of holes in a way that nucleic acid in each hole of the one sample tray and a first reagent are distributed into a plurality of holes of the one detection tray; and
    wherein the nucleic acid detection device is configured to perform, on the nucleic acid detection machine platform, nucleic acid detection on the one detection tray.

2. The automatic nucleic acid detection system of claim 1, wherein a size of the one sample tray is the same as a size of the one detection tray.

3. The automatic nucleic acid detection system of claim 1, wherein the computer device is configured to control the second robotic arm to correspondingly distribute a plurality of nucleic acids in a plurality of holes in the one sample tray into a plurality of holes in the one detection tray simultaneously for multiple times.

4. The automatic nucleic acid detection system of claim 1, wherein a scanner and a first robotic arm are disposed on the nucleic acid extraction machine platform,
    the scanner is configured to confirm an identification of a specimen container, wherein the specimen container contains the specimen or one of the plurality of specimens, and
    the computer device is configured to control the first robotic arm to place the specimen in the specimen container in the one sample tray, when the identification of the specimen container is confirmed.

5. The automatic nucleic acid detection system of claim 4, wherein a bottle cap separator is disposed on the nucleic acid extraction machine platform, and the bottle cap separator is configured to open a cap of the specimen container before placing the specimen in the specimen container in the one sample tray.

6. The automatic nucleic acid detection system of claim 5, wherein a bottle cap detector is disposed on the nucleic acid extraction machine platform, and the bottle cap detector is configured to monitor whether the cap of the specimen container is successfully opened.

7. The automatic nucleic acid detection system of claim 1, wherein a centrifuge is disposed on the nucleic acid distribution machine platform, and the centrifuge is configured to mix, on the nucleic acid distribution machine platform, the nucleic acid and the first reagent in each hole in the one detection tray in a centrifugal manner.

8. The automatic nucleic acid detection system of claim 7, wherein when a volume of the nucleic acid in each hole in the one detection tray is less than a preset value, the centrifuge mixes the nucleic acid and the first reagent in each hole in the one detection tray only in the centrifugal manner.

9. The automatic nucleic acid detection system of claim 1, wherein the computer device is further configured to control the second robotic arm to add a second reagent into each hole in the one detection tray that contains the nucleic acid and the first reagent;
    wherein the automatic control subsystem further comprise an optical detector, and the optical detector is configured to monitor whether the nucleic acid, the first reagent, and the second reagent are successfully added into each hole in the one detection tray.

10. The automatic nucleic acid detection system of claim 1, wherein the automatic control subsystem is further configured to seal each hole in the one detection tray that contains the nucleic acid and the first reagent by a cap, a film, or a sticker.

11. The automatic nucleic acid detection system of claim 1, wherein the automatic control subsystem further comprise an optical detector, and the optical detector is configured to monitor whether each hole in the one detection tray contains the nucleic acid and the first reagent.

12. The automatic nucleic acid detection system of claim 1, wherein a temperature of each of a specimen placement area on the nucleic acid extraction machine platform, a detection tray placement area and a first reagent placement area on the nucleic acid distribution machine platform is maintained within a preset range.

13. An automatic nucleic acid distribution system, comprising:
    a nucleic acid distribution machine platform, wherein a second robotic arm is disposed on the nucleic acid distribution machine platform; and
    an automatic control subsystem, comprising a computer device, the second robotic arm, and a transmission device and being connected with the nucleic acid distribution machine platform,
    wherein the automatic control subsystem is configured to provide a sample tray for the nucleic acid distribution machine platform via the transmission device, wherein the sample tray contains nucleic acid of one or a plurality of specimens; and wherein the computer device is configured to control the second robotic arm to perform, on the nucleic acid distribution machine platform, nucleic acid distribution from one sample tray having a fewer number of holes to one detection tray having a greater number of holes in a way that nucleic acid in each hole of the one sample tray and a first reagent are distributed into a plurality of holes in the one detection tray.

14. The automatic nucleic acid distribution system of claim 13, wherein a size of the one sample tray is the same as a size of the one detection tray.

15. The automatic nucleic acid distribution system of claim 13, wherein the computer device is configured to control the second robotic arm to correspondingly distribute a plurality of nucleic acids in a plurality of holes in the one sample tray into a plurality of holes in the one detection tray simultaneously for multiple times.

16. The automatic nucleic acid distribution system of claim 13, wherein a centrifuge is disposed on the nucleic acid distribution machine platform, and the centrifuge is configured to mix, on the nucleic acid distribution machine platform, the nucleic acid and the first reagent in each hole in the one detection tray in a centrifugal manner.

17. The automatic nucleic acid distribution system of claim 16, wherein when a volume of the nucleic acid in each hole in the one detection tray is less than a preset value, the centrifuge mixes the nucleic acid and the first reagent in each hole in the one detection tray only in the centrifugal manner.

18. The automatic nucleic acid distribution system of claim 13, wherein the computer device is further configured to control the second robotic arm to add a second reagent into each hole in the one detection tray that contains the nucleic acid and the first reagent; and wherein the automatic control subsystem further comprise an optical detector, and the optical detector is configured to monitor whether the nucleic acid, the first reagent, and the second reagent are successfully added into each hole in the one detection tray.

19. The automatic nucleic acid distribution system of claim 13, wherein the automatic control subsystem is further configured to seal each hole in the one detection tray that contains the nucleic acid and the first reagent by a cap, a film, or a sticker.

20. The automatic nucleic acid distribution system of claim 13, wherein the automatic control subsystem further comprise an optical detector, and the optical detector is configured to monitor whether each hole in the one detection tray contains the nucleic acid and the first reagent.

* * * * *